US008700159B2

(12) United States Patent
Rundle et al.

(10) Patent No.: US 8,700,159 B2
(45) Date of Patent: Apr. 15, 2014

(54) METHODS OF MANUFACTURING AN IMPLANTABLE PULSE GENERATOR

(71) Applicant: Pacesetter, Inc., Sylmar, CA (US)

(72) Inventors: Nicholas A. Rundle, Madison, WI (US); Reza Imani, Moorpark, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/014,166

(22) Filed: Aug. 29, 2013

(65) Prior Publication Data

US 2014/0000107 A1 Jan. 2, 2014

Related U.S. Application Data

(62) Division of application No. 13/413,478, filed on Mar. 6, 2012, now Pat. No. 8,560,071, which is a division of application No. 12/182,097, filed on Jul. 29, 2008, now Pat. No. 8,155,743.

(51) Int. Cl.
*A61N 1/375* (2006.01)

(52) U.S. Cl.
USPC .......................................................... 607/36

(58) Field of Classification Search
CPC ... A61N 1/3752; A61N 1/3754; A61N 1/375; A61N 1/378
USPC .......................................................... 607/36
See application file for complete search history.

(56) References Cited

U.S. PATENT DOCUMENTS

| 5,897,267 | A  | 4/1999  | Poolman         |
|-----------|-----|---------|-----------------|
| 6,115,634 | A  | 9/2000  | Donders et al.  |
| 6,240,317 | B1 | 5/2001  | Villaseca et al.|
| 7,038,900 | B2 | 5/2006  | Stevenson et al.|
| 7,310,216 | B2 | 12/2007 | Stevenson et al.|
| 7,601,033 | B2 | 10/2009 | Ries et al.     |
| 8,000,804 | B1 | 8/2011  | Wessendorf      |
| 8,155,743 | B2 | 4/2012  | Rundle et al.   |
| 2004/0215280 | A1 | 10/2004 | Dublin et al. |
| 2007/0043399 | A1 | 2/2007  | Stevenson et al. |
| 2007/0260287 | A1 | 11/2007 | Receveur      |
| 2009/0187229 | A1 | 7/2009  | Lavie          |

FOREIGN PATENT DOCUMENTS

| EP | 1176903 B1    | 6/2006 |
| WO | 2007050002 A1 | 5/2007 |

OTHER PUBLICATIONS

Restriction Requirement, mailed Feb. 21, 2013—Parent U.S. Appl. No. 13/413,478.
NonFinal Office Action, mailed Mar. 19, 2013—Parent U.S. Appl. No. 13/413,478.
Notice of Allowance, mailed Aug. 20, 2013—Parent U.S. Appl. No. 13/413,478.

*Primary Examiner* — Carl H Layno
*Assistant Examiner* — Paula J Stice

(57) ABSTRACT

Disclosed herein is an implantable pulse generator feedthru configured to make generally planar electrical contact with an electrical component housed within a can of an implantable pulse generator. The feedthru may include a feedthru housing including a header side and a can side, a core within the feedthru housing, a generally planar electrically conductive interface adjacent the can side, and a feedthru wire extending through the core. The feedthru wire may include an interface end and a header end, wherein the header end extends from the header side and the interface end is at least one of generally flush with the generally planar interface and generally recessed relative to the generally planar interface.

10 Claims, 10 Drawing Sheets

METHODS OF MANUFACTURING AN IMPLANTABLE PULSE GENERATOR

CROSS REFERENCE TO RELATED APPLICATIONS

This application is a division of U.S. patent application Ser. No. 13/413,478, filed Mar. 6, 2012, now U.S. Pat. No. 8,560,071, which is a division of U.S. patent application Ser. No. 12/182,097, filed Jul. 29, 2008, now U.S. Pat. No. 8,155,743.

FIELD OF THE INVENTION

The present invention relates to medical apparatus and methods. More specifically, the present invention relates to implantable pulse generator feedthrus and methods of manufacturing and installing feedthrus.

BACKGROUND OF THE INVENTION

Implantable pulse generators 5, such as defibrillators, pacemakers or implantable cardioverter defibrillators ("ICD"), are used to provide electrotherapy to cardiac tissue via implantable medical leads 7. As shown in FIGS. 1A and 1B, which are isometric views of various embodiments of a pulse generator 5, a common pulse generator 5 may include a header 10 and a can or housing 15. The can 15 is typically made of titanium or another biocompatible metal and serves as a hermetically sealed enclosure for the pulse generator's electronic components (e.g., output flex, hybrid, or various other electronic components or circuit boards, printed circuit boards ("PCB"), etc.) contained in the can 15.

As indicated in FIG. 1A, the header 10 may include connector blocks 20 and a molded portion 25 (shown in phantom) that encloses the blocks 20. Each block 20 includes an opening 35 configured to receive therein and mate with a connector end 40 of a lead proximal end 45, thereby forming an electrical connection between the connector block 20 and the lead connector end 40 and mechanically securing the proximal end 45 of the lead 7 to the header 10 of the pulse generator 5.

As illustrated in FIG. 1B, the header 10 may also include an RF antenna 37 that is enclosed by the molded portion 25. One end of the RF antenna 37 may be physically and electrically connected to the can 15 via an RF tab or anchor 38 on a header side of the can 15. The other end of the RF antenna 37 is physically and electrically connected to a feedthru wire 60 of the feedthru 55. The RF antenna 37 allows the implantable pulse generator 5 to wirelessly communicate with a programmer, such as a computer (not shown). The RF antenna 37 may be coupled to the feedthru 55 and the tab 38 by welding, soldering, brazing, etc.

The header-molded portion 25 informed of a polymer material. Passages 50 (shown in phantom in FIG. 1A) extend from the exterior of the molded portion 25 to the openings 35 in the blocks 20, providing a pathway for the lead distal ends 40 to pass through the molded portion 25 and enter the openings 35.

As can be understood from FIGS. 1A and 1B, the can 15 may include a feedthru 55 that may electrically connect via a feedthru wire 60 to an RF antenna 37, as shown in FIG. 1B, and feedthrus 55 that may electrically connect with respective connector blocks 20 in the header 10, as shown in FIG. 1A.

As indicated in FIG. 2, which is a cross-sectional elevation of one of the feedthrus 55 of FIG. 1A, the feedthru 55 extends through the wall 65 of the can 15. The feedthru wire 60 extends through the feedthru 55 and projects from the header and can sides 70, 75 of the feedthru 55. The feedthru 55 provides a hermetically sealed pathway for the feedthru wire 60 to extend between the electronic components 80 housed within the can 15 and a connector block 20 or RF antenna 37 of the header 10.

As shown in FIG. 2, the electronic components 80 housed within the can wall 65 may include or be mounted on a PCB 85. The term "printed circuit board", "PCB" or "circuit board" as used herein describes a component 80 that is often planar in configuration and may be used to mechanically support and electrically connect the electronic components 80 populating the PCB 85. Electrically conductive pathways or traces on the PCB 85 may provide the electrical connections between the electronic components 80 populating the PCB 85. The electrically conductive pathways or traces may be etched from sheets of electrically conductive metal (e.g., copper, gold, etc.) laminated onto a non-conductive substrate.

As illustrated in FIG. 2, the feedthru wire 60 extending from the feedthru can side 75 extends through a through-hole 90 in the PCB 85. Once extended through the PCB through-hole 90, the feedthru wire 60 is soldered in place. This through-hole method of connecting the feedthru wire 60 to the PCB 85 is disadvantageous for at least a couple of reasons. First, because the feedthru wire 60 extends through both sides of the PCB 85, both sides of the PCB 85 in the vicinity of the wire 60 must be kept free of electronic components, which waste space within the can 15. Second, the feedthru wire 60 has to be overly long to allow it to pass completely through the PCB 85, which adds to the material cost of the pulse generator 5. Third, aligning the wire 60 with and passing the wire 60 through the through-hole 90 is time consuming, which adds to the assembly time associated with assembling the pulse generator 5.

There is a need in the art for a feedthru that reduces the manufacturing costs associated with manufacturing a pulse generator. There is also a need in the art for a more economical method of electrically coupling a feedthru wire to the electronic components housed within the can.

BRIEF SUMMARY OF THE INVENTION

Disclosed herein is an implantable pulse generator feedthru configured to make generally planar electrical contact with an electrical component housed within a can of an implantable pulse generator. In one embodiment, the feedthru includes a feedthru housing including a header side and a can side, a core within the feedthru housing, a generally planar electrically conductive interface adjacent the can side, and a feedthru wire extending through the core. The feedthru wire includes an interface end and a header end, wherein the header end extends from the header side and the interface end is at least one of generally flush with the generally planar interface and generally recessed relative to the generally planar interface.

Disclosed herein is an implantable pulse generator. In one embodiment, the pulse generator includes a header, a can, a feedthru, and an electrical component housed within the can. The feedthru extends between the header and can and includes a header side, a first generally planar electrically conductive interface opposite the header side, and a feedthru wire extending through the feedthru from the first interface to project from the header side into the header. The electrical component includes a second generally planar electrically conductive interface. The first and second interfaces are in electrical contact.

Disclosed herein is a method of manufacturing an implantable pulse generator. In one embodiment, the method includes: providing a feedthru including a generally planar electrically conductive interface; providing an electrical component including a generally planar electrically conductive interface; and placing the interfaces in physical contact with each other, for example, via a pick-and-place process.

Disclosed herein is an implantable pulse generator. In one embodiment, the implantable pulse generator includes a feedthru and an electrical component. The feedthru includes a generally planar electrically conductive interface. The electrical component includes a generally planar electrically conductive interface in abutting contact with the feedthru interface. The abutting contact may be achieved via a pick-and-place process.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1A:
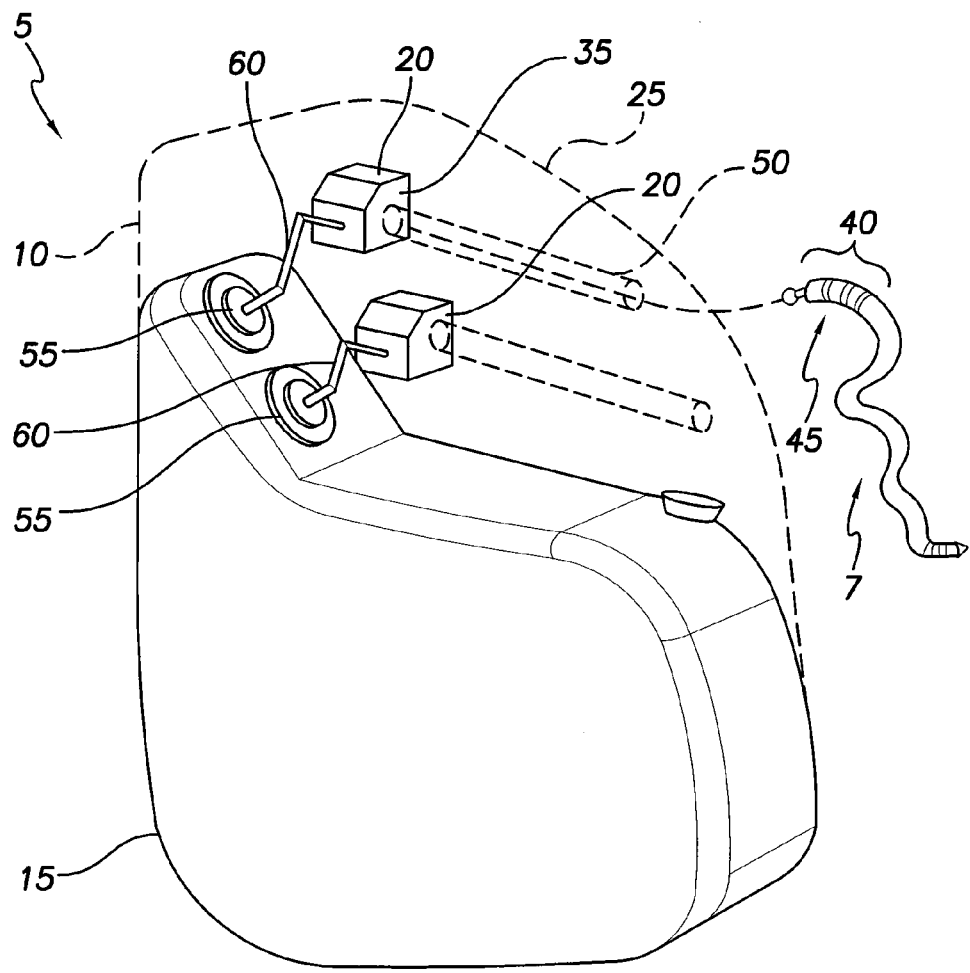
FIG. 1A is an isometric view of a prior art pulse generator illustrating feedthrus electrically coupled to lead connector blocks.
Figure 1B:
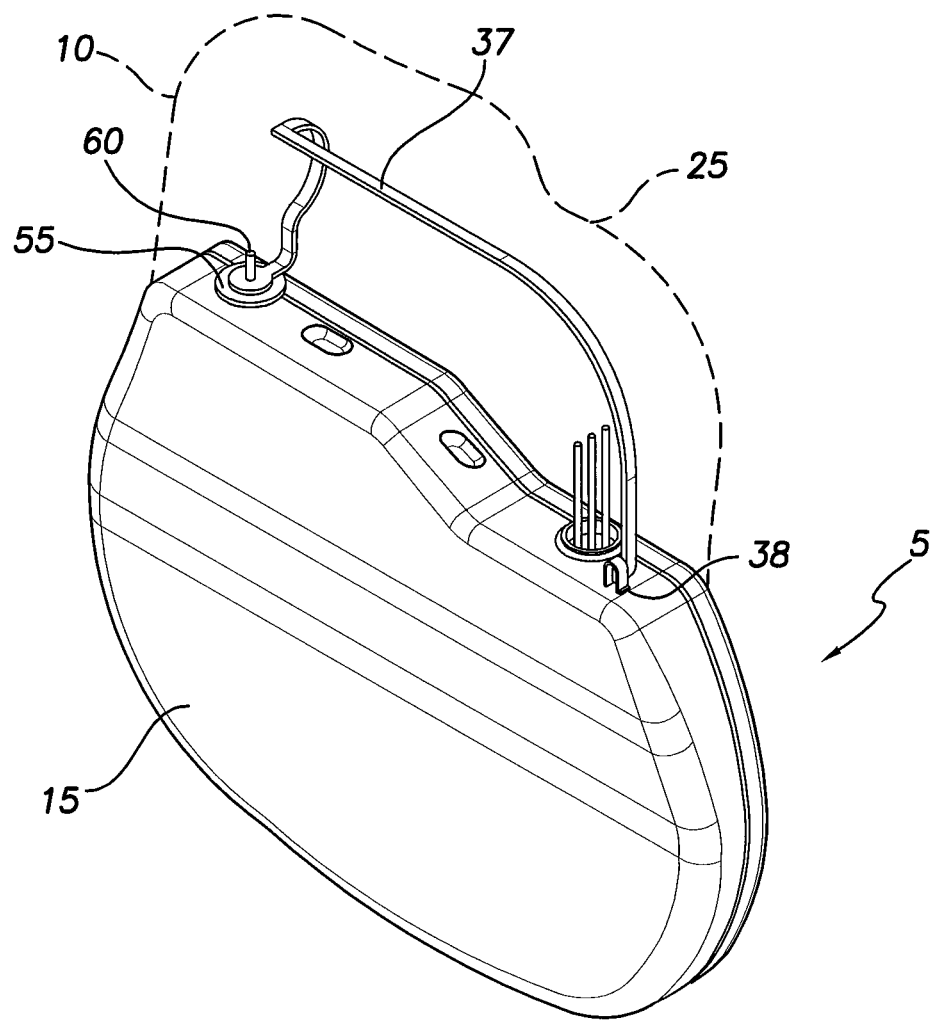
FIG. 1B is an isometric view of a prior art pulse generator illustrating a feedthru electrically coupled to a RF antenna.

The present disclosure describes a feedthru 155 of an implantable pulse generator 5 such as a pacemaker, defibrillator or ICD. The feedthru 155 disclosed herein provides an electrically insulated passageway through which the feedthru wire 160 can pass through the can wall 65. The feedthru 155 also prevents RF radiation from escaping the feedthru wire 160 and interfering with other electrical components of the pulse generator 5. In one embodiment, when the feedthru 155 is employed for the purpose depicted in FIG. 1A, the feedthru 155 will allow the feedthru wire 160 to pass through the can wall 65 as the feedthru wire 160 extends between the blocks 20 of the header 10 and the electrical components enclosed within the can 15. In some embodiments, when the feedthru 155 is employed for the purpose depicted in FIG. 1B, the feedthru wire 160 of the feedthru 155 may be connected to an RF antenna 37 to couple electrical components within the can 15 to the antenna 37 to promote wireless communication between the implantable pulse generator 5 and a programmer, such as a computer.

The feedthru 155 disclosed herein includes an interface 190 on the can side 175 of the feedthru 155 that is configured to facilitate the electrical connection of the feedthru 155 to an electrical component 180 via pick-and-place manufacturing methods, wherein the electrical component 180 is housed or to be housed within the walls 65 of the can 15. The feedthru 155 reduces manufacturing costs by reducing the amount of wire used for a feedthru wire 160 and increasing production speed via a higher degree of automation. Additionally, the feedthru 155 saves space within the pulse generator 5 by reducing the space necessary for the attachment of the feedthru wire 160 to a PCB 185 or other feature of the electrical components 180.

Figure 3:
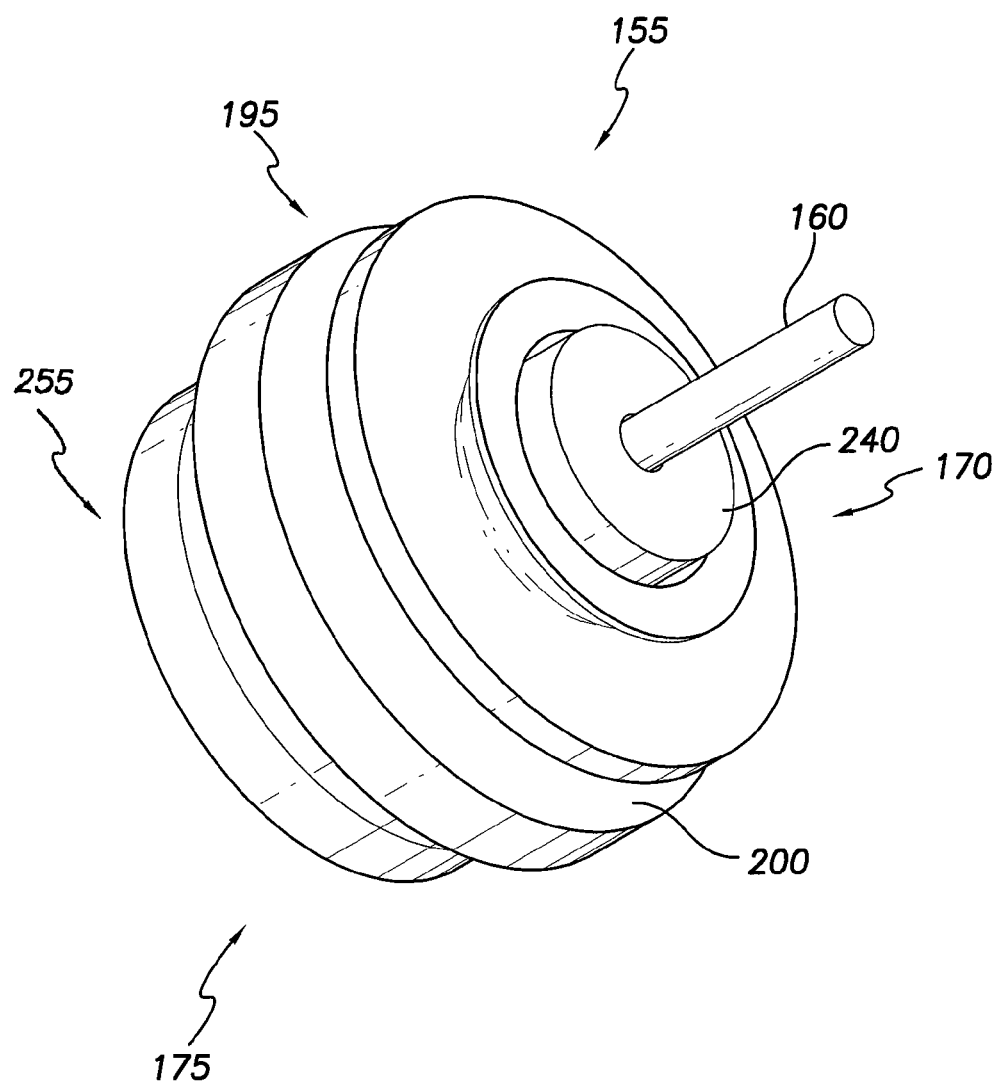
FIG. 3 is a top isometric view of the feedthru of the present disclosure.
Figure 4:
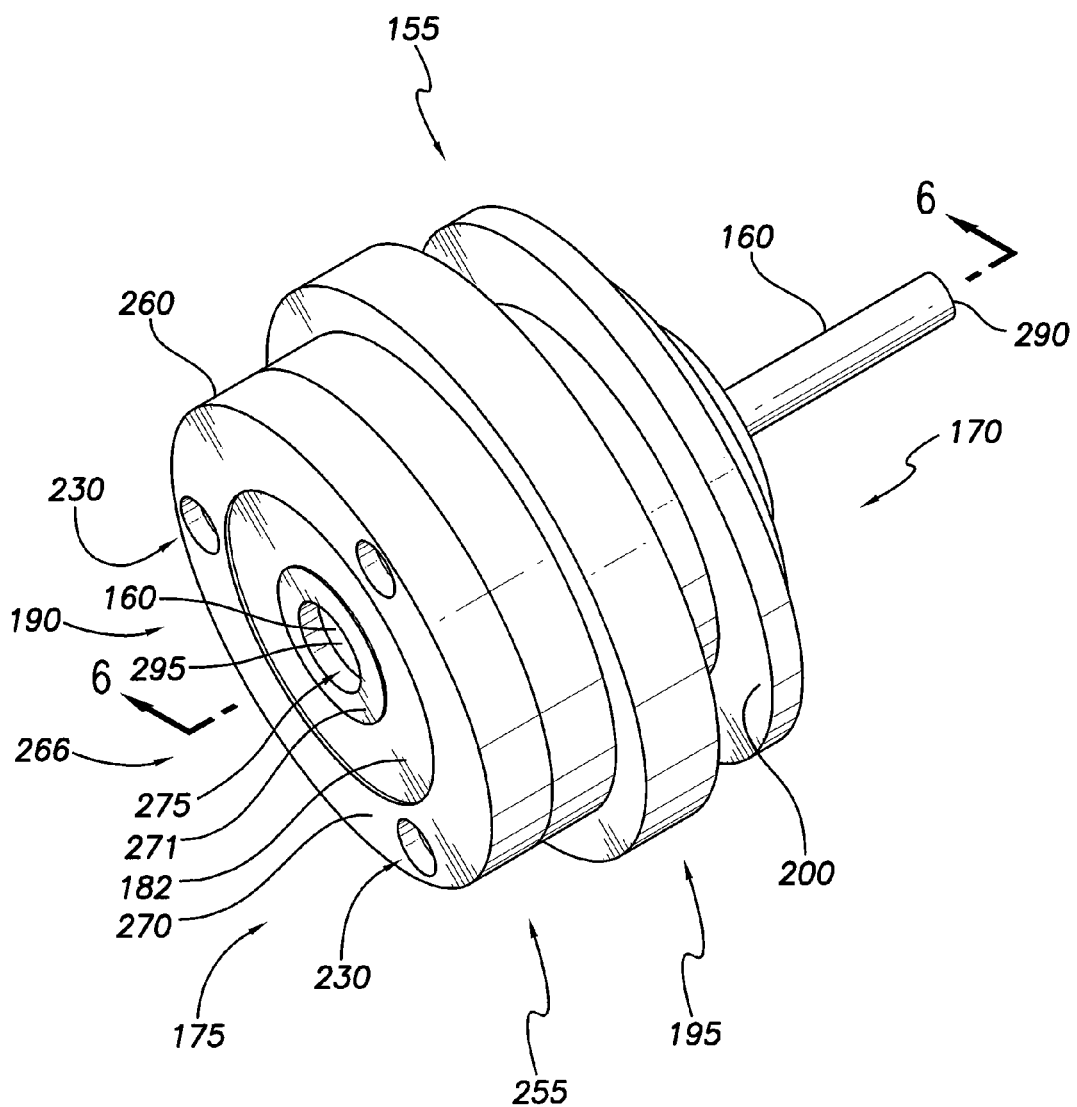
FIG. 4 is a bottom isometric view of the feedthru of FIG. 3.
Figure 5:
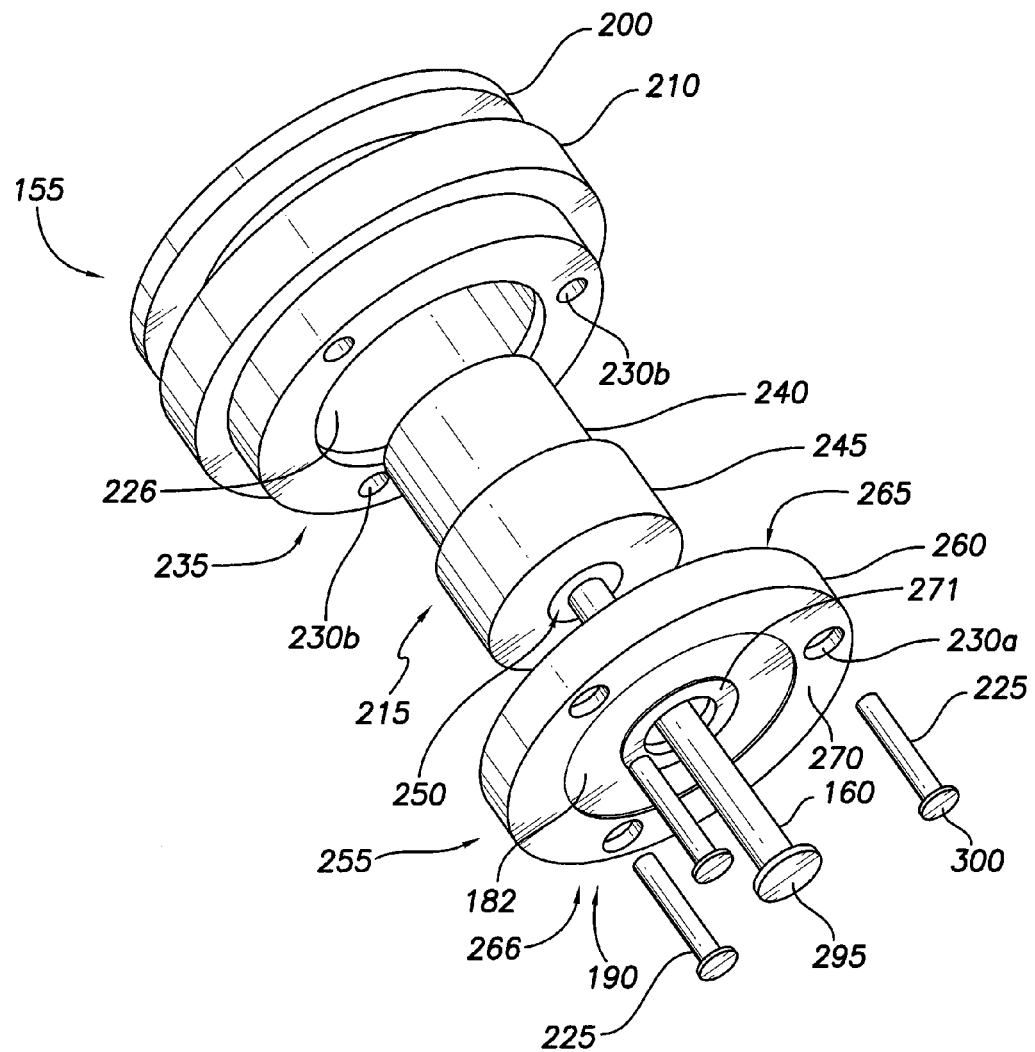
FIG. 5 is an exploded bottom isometric view of the feedthru of FIG. 3.
Figure 6:
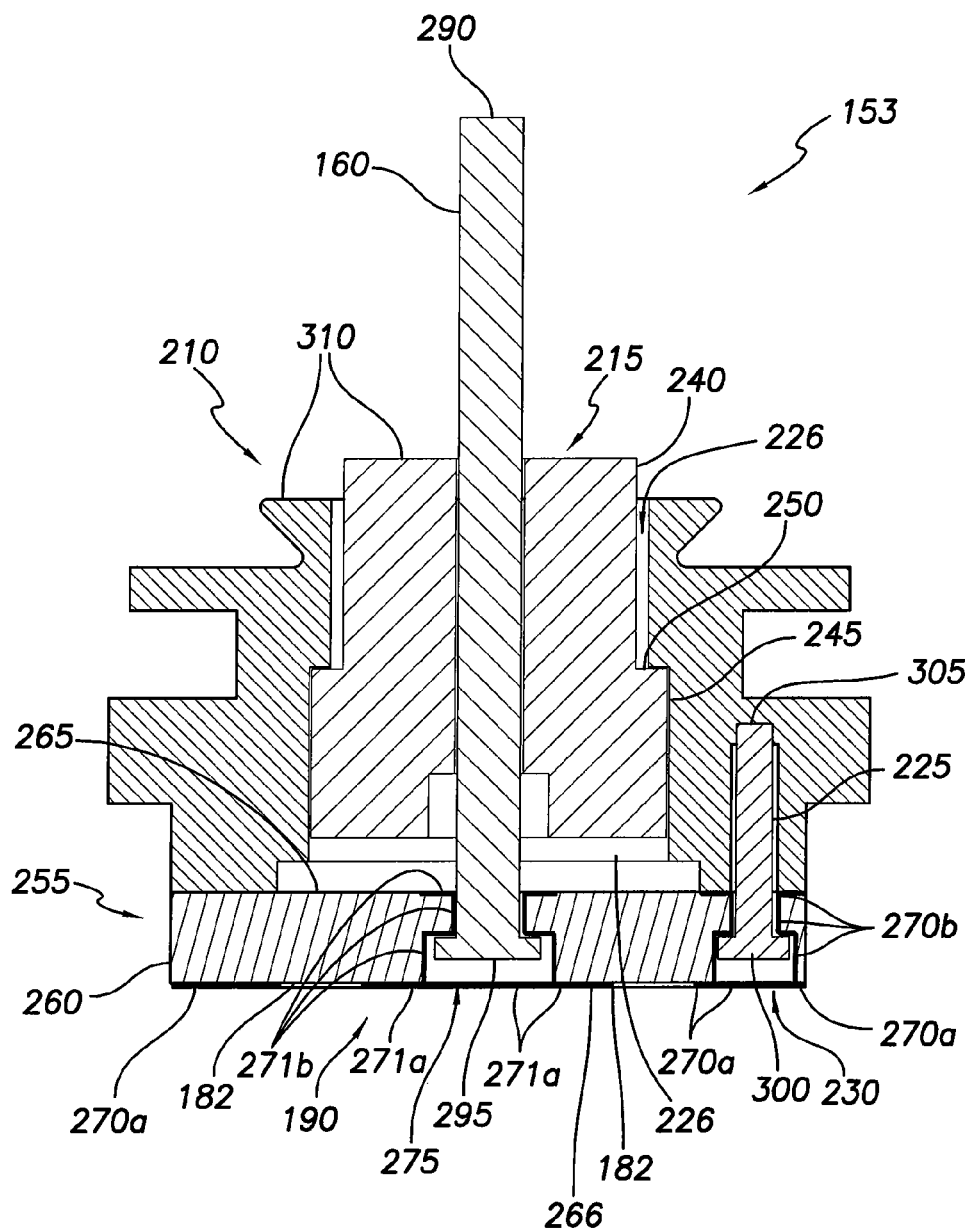
FIG. 6 is a longitudinal cross-section of the feedthru as taken along section line 6-6 of FIG. 4.

For a detailed discussion of an embodiment of the feedthru 155 disclosed herein, reference is first made to FIGS. 3-6. FIGS. 3-5 are, respectively, top isometric, bottom isometric, and exploded bottom isometric views of the feedthru 155. FIG. 6 is a longitudinal cross-section of the feedthru 155 as taken along section line 6-6 of FIG. 4, which extends along a longitudinal axis of the feedthru 155 and the feedthru wire 160 extending therethrough.

As shown in FIGS. 3-4, in one embodiment, the feedthru 155 includes a header side 170, a can side 175, and a circular side 195 that may vary in diameter such that the circular side 195 has the appearance of being assembled from a plurality of stacked circular rings having different diameters. The varying diameter of the circular side 195 may define a groove or slot 200 that receives the wall 65 of the can 15 when the feedthru 155 is assembled into the can 15. The feedthru wire 160 extends from the header side 170, but is generally flush with, or recessed relative to, the interface 190 on the can side 175. In one embodiment, the feedthru 155 is unipolar and may have a single feedthru wire 160. In some embodiments, the feedthru 155 may be multipolar and may have multiple feedthru wires 160.

As can be understood from FIGS. 4-6, the feedthru 155 includes the feedthru wire 160, a feedthru housing 210, a core 215, a can-side end piece or plate 255, and ground wires 225. The housing 210 includes the circular side 195, a groove or slot 200, a central or core-receiving bore 226 and ground wire-receiving bore 230. The housing 210 may be machined, molded or otherwise formed to fit the space and design constraints of a printed circuit board of an implantable pulse generator 5. The housing may be titanium, a titanium alloy, or nickel.

The outer circumference of the housing 210 is defined by the circular side 195 and includes the groove or slot 200. The central bore 226 of the housing 210 extends axially through the housing 210 and may have a stepped cylindrical construction. The central bore 226 of the housing 210 defines a passageway to receive the core 215.

As shown in FIG. 5, the bottom or can side 235 of the housing 210 includes ground wire bores 230*b*. The ground wire bores 230*b* generally correspond to ground wire bores 230*a* in the plate 255 to form continuous ground wire bores 230 that extend through the plate 255 and into the housing 210. The ground wire bores 230*b* in the plate may be a counterbore, that is, a cylindrical flat bottomed opening which enlarges another opening.

As indicated in FIGS. 5 and 6, the core 215 includes a first cylindrical portion 240, a second cylindrical portion 245 and a feedthru wire bore 250 extending longitudinally therethrough. The bore 250 receives the feedthru wire 160 and provides an insulating passageway for the feedthru wire 160 to extend through the core 215 and, as a result, the feedthru 155. The core 215 may be ceramic.

The outer circumferential surface of the core 215 is cylindrically stepped such that it has a first cylindrical portion 240 and a second cylindrical portion 245 with a diameter greater than the diameter of the first cylindrical portion 240.

As can be understood from FIGS. 3 and 6, the core 215 is received in the central bore 226 of the housing 210 such that the second cylindrical portion 245 abuts a step 250 in the central bore 226 of the housing 210, and the first cylindrical portion 240 is exposed at the header side 170 of the feedthru 155.

As illustrated in FIGS. 5 and 6, the plate 255 includes an outer circumferential surface 260, a core side 265, and the interface side 266. The outer circumferential surface 260 of the plate 255 and the outer circumference of the housing 210 define the outer circumference of the feedthru 155. The body of the plate 255 can be any insulating material, such as ceramic, that is brazable.

As depicted in FIGS. 4 and 6, the core side 265 of the plate 255 abuts against the can side 235 of the housing 210 when the feedthru 155 is assembled. In an alternative embodiment, the core side 265 of the plate 255 is adapted to receive the housing 210. In other words, the bottom or can side 235 of the housing 210 is received in the core side 265 of the plate 255.

As illustrated in FIGS. 5 and 6, the interface side 266 includes the planar electrically conductive interface 190 having electrical traces 270, 271 with bores 230, 275 defined therein. At least one bore 230 is adapted to receive a ground wire 225 and the ground wire 225 electrically connects the outer or ground electrical trace 270 with the housing 210. In one embodiment, there are three bores 230 located at the outer or ground electrical trace 270. In alternative embodiments, there may be four or more bores 230 or there may be two or fewer bores 230, each having a respective ground wire 225 located therein.

In one embodiment, the traces 270, 271 of the planar electrically conductive interface 190 may be in the form of two concentric rings. For example, as indicated in FIGS. 4 and 5, the inner trace 271 may be in the form of a solid or continuous disk or circle or in the form of a continuous ring. The outer trace 270 is radially spaced apart from the inner trace 271 such that the insulative material of the body of the plate 255 is exposed and a ring space 182 insulates the traces 270, 271 from each other. The outer trace 270 may be in the form of a continuous ring. The electrically conductive traces 270, 271 may be formed of any electrically conductive material (e.g. gold plated with a nickel base, copper, tungsten, etc.) capable of being formed into a trace via any method including photo etching, deposition, etc. In alternative embodiments, there may be more or less than two traces 270, 271 or the traces may not be concentric with respect to each other. The traces 270, 271 may also be non-continuous. For example, the traces 270, 271 may be segmented arcuate portions forming a segmented circular trace. The traces 270, 271 may also have other shapes besides arcuate or curved shapes. For example, the shapes may be rectangular or linear.

As shown in FIGS. 4, 5 and 6, the feedthru wire 160 includes a header end 290 and a can end 295. As can be understood from FIGS. 4-6, the feedthru wire 160 is received in the center or feedthru wire bore 275 at the center of the plate 255 such that the can end 295 of the feedthru wire 160 is generally flush with, or recessed relative to, the interface side 266 of the plate 255. The feedthru wire 160 is generally cylindrical and is flattened or stamped at its can end 295 to form a head 295. In alternative embodiments, the can end 295 of the feedthru wire 160 may be another configuration besides flattened or stamped. Upon placement (e.g. via pick and place technology) or connection onto the printed circuit board, the feedthru wire 160 will be in electrical connection or electrical communication with the other electrical components. In one embodiment, the feedthru wire 160 is an RF lead such that the feedthru 155 may be employed for the purpose depicted in FIG. 1B. In one embodiment, the feedthru wire 160 is a connector block lead such that the feedthru 155 may be employed for the purpose depicted in FIG. 1A. The feedthru wire 160 may be made of Pt/Ir wire, such as 90% Pt/10% Ir wire, or other electrically conductive materials.

As indicated in FIGS. 5 and 6, each ground wire 225 includes a plate end 300 and a housing end 305. As can be understood from FIGS. 4 and 5, each ground wire 225 is received in a ground wire bore 230 such that the plate end 300 of the ground wire 225 is generally flush, or recessed relative to, the plate 255. In one embodiment, the ground wire 225 is generally cylindrical and is flattened or stamped at its plate end 300 to form a head 300. In alternative embodiments, the plate end 300 may be other configurations besides stamped or flattened. The ground wire 225 may be made of Pt/Ir wire, such as 90% Pt/10% Ir wire, or other electrically conductive materials.

As can be understood from FIGS. 3, 4 and 6, to assemble the feedthru 155, the housing 210 and the core 215 may be connected by brazing, welding, or soldering to form a housing-core assembly or complex 310. The plate 255 may be connected to the housing-core assembly 310 by brazing, soldering, or welding. The ground wires 225 and the feedthru wire 160 may be placed through the bores 230, 275 in the plate 255 and housing-core assembly 310 until the ends 300, 295 of the wires 225, 160 are generally flush, or recessed relative to the openings 230, 275. The ends 300, 295 of the wires 225, 160 may also be connected to the recessed openings of the bores 230, 275 by brazing, soldering, or welding.

As can be understood from FIG. 6, there is an open area 320 between the can side of the core 215, the core side of the plate 255 and the internal circumference of the central bore 226 of the housing 210. This open area 320 may provide for ease of the feedthru assembly process.

As indicated in FIG. 6, the feedthru trace 271 may include planar portions 271a that are generally planar and flush with the planar face of the interface side 266. The feedthru trace 271 may also include a recessed portion 271b that lines the bore 275 with trace material. In some embodiments, the trace material may even line the recess opening and shaft portion of the bore 275 as it extends through the plate 255. The trace material may even extend out of the bore 275 on the core side 265 of the bore 275 to define a ring of trace material about the opening of the bore 275 on the core side 265.

As shown in FIG. 6, the conductor trace 270 may include planar portions 270a that are generally planar and flush with the planar face of the interface side 266. The conductor trace 270 may also include a recessed portion 270b that lines the bore 230 with trace material. In some embodiments, the trace material may even line the recess opening and shaft portion of the bore 230 as it extends through the plate 255. The trace material may even extend out of the bore 230 on the core side 265 of the bore 230 to define a ring of trace material about the opening of the bore 230 on the core side 265.

Figure 7A:
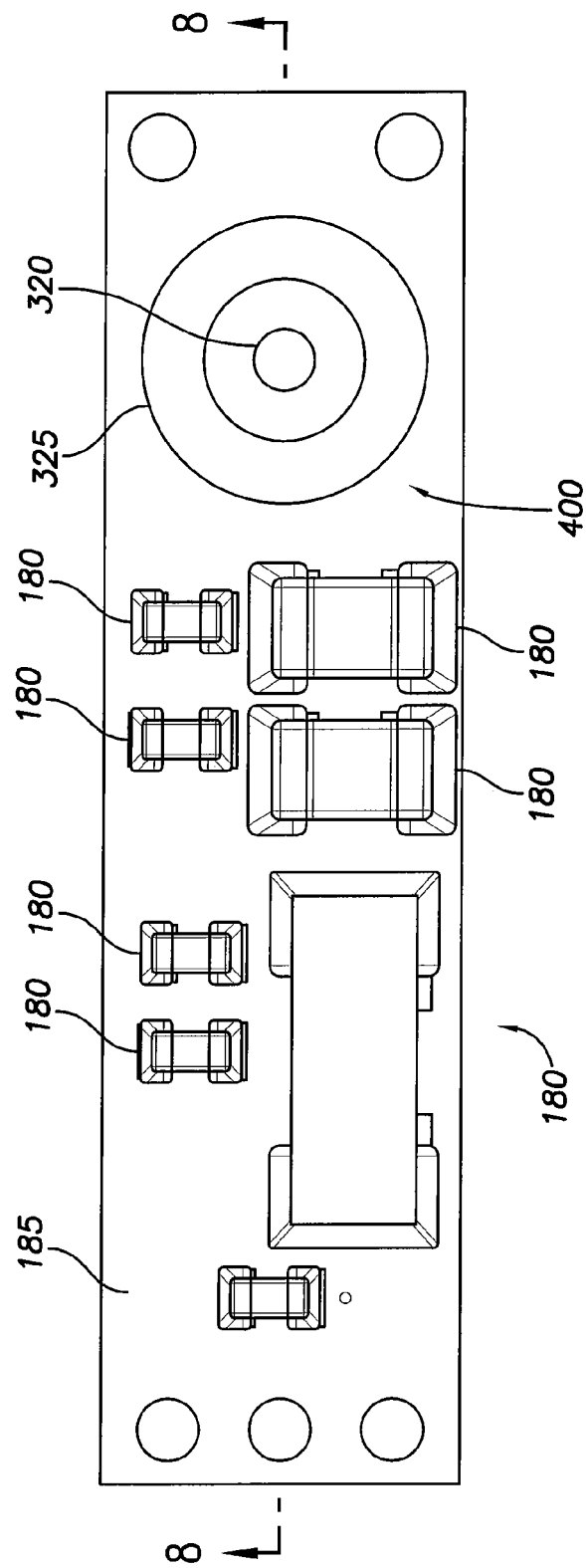
FIG. 7A is a top plan view of a printed circuit board, wherein the feedthru of FIG. 3 is hidden and multiple conductive traces are shown.
Figure 7B:
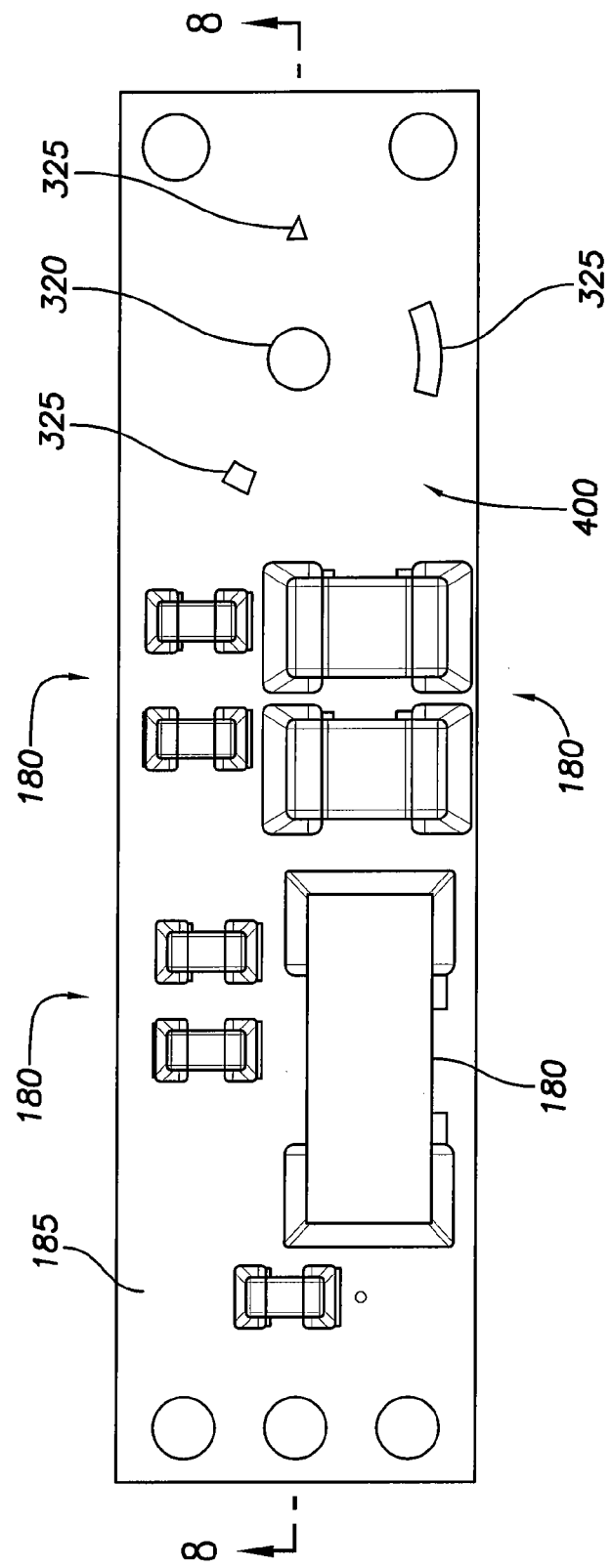
FIG. 7B is a top plan view of the printed circuit board of FIG. 7A, wherein the feedthru is hidden and alternative conductive traces are shown.

For a discussion of the location and orientation of the feedthru 155 on a printed circuit board 185 housed within the can 15 of an implantable pulse generator 5, reference is now made to FIGS. 7A and 7B. FIG. 7A is a top plan view of a printed circuit board 185, wherein the feedthru 155 of FIG. 3 is hidden and multiple conductive traces 320, 325 are shown. FIG. 7B is a top plan view of the printed circuit board 185 of FIG. 7A, wherein the feedthru 155 is hidden and alternative conductive traces 325 are shown.

As shown in FIG. 7A and with reference to FIG. 4, the printed circuit board 185 includes electrical components 180 and power and ground conductive traces 320, 325 that form a planar electrically conductive interface 400 of the board 185. The conductive traces 320, 325 of the board interface 400 correspond to the power and ground conductive traces 271, 270 found on the planar electrically conductive interface 190 at the interface side 266 of the plate 255. In one embodiment, all traces 271, 270, 320, 325 are generally continuous rings or disk shaped configurations. In one embodiment, the feedthru 155 is aligned with respect to each respective conductive trace to maintain an electrical connection between the ground traces 270, 325 of the feedthru 155 and the printed circuit board 185, and the power traces 271, 320 of the printed circuit board 185 and the feedthru 155.

As can be understood from FIG. 7B, the feedthru conductive traces 271, 270 may be aligned with alternatively shaped conductive traces 320, 325 on the printed circuit board 185. That is, the power conductive trace 271 that places the feedthru wire 160 in electrical communication with the power side of the board 185 is aligned with the power conductive trace 320. The ground conductive trace 270 that places the ground wires 225 in electrical communication with the ground side of the board 185 may be aligned with a ground conductive trace 325 of any shape or size such that the electrical connection between the feedthru wire 160 and the printed circuit board 185 is maintained. For example, the ground conductive traces 325 of the board 185 could be segmented such that it is one or more arcuate segments or any other shape or configuration, and the ground conductive trace 270 of the feedthru 155 is a continuous circle or ring. In other embodiments, the reverse configuration is the case, with the ground trace 270 of the feedthru 155 segmented and the ground trace 325 of the board 185 a continuous ring.

Figure 8:
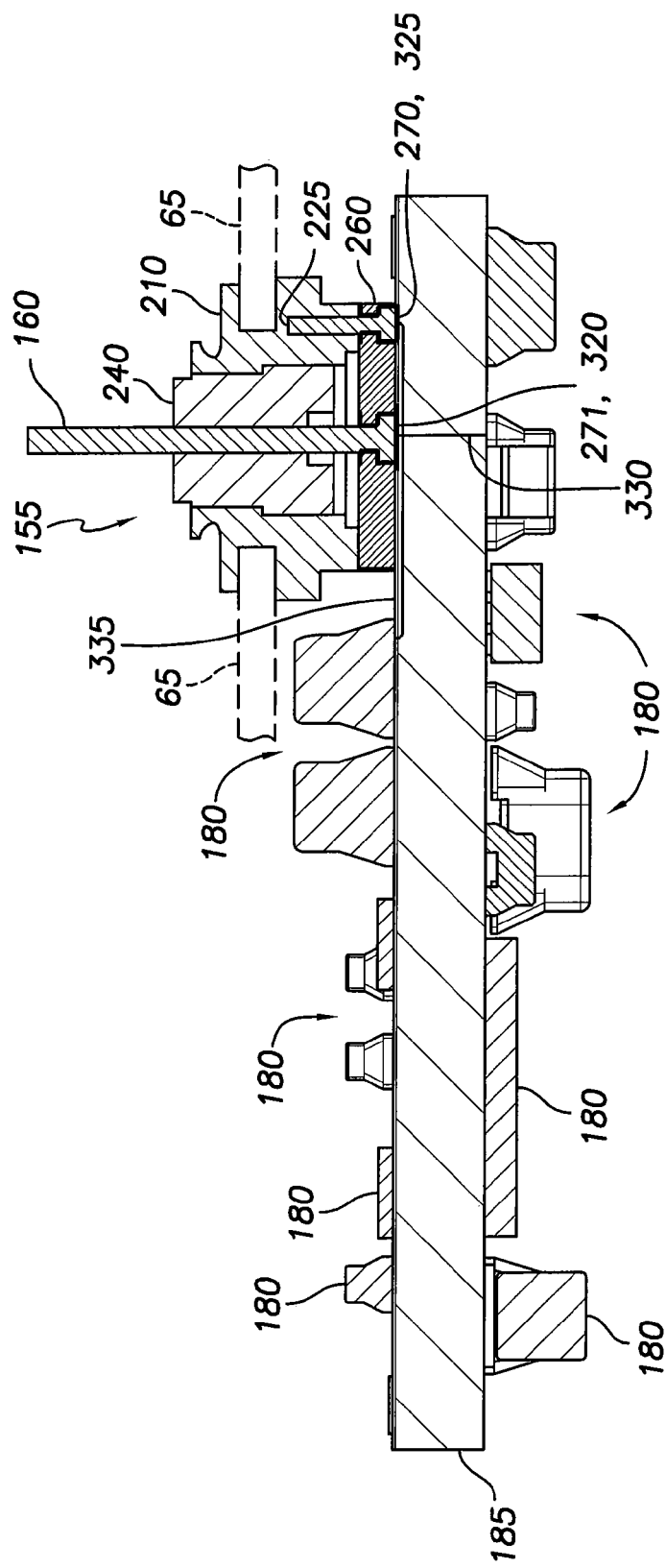
FIG. 8 is a longitudinal cross-section of the printed circuit board as taken along section line 8-8 in FIG. 7A, wherein the feedthru is shown connected to the board.

For a discussion of the feedthru 155 and its relationship to the printed circuit board 185, reference is now made to FIG. 8. FIG. 8 is a longitudinal cross-section of the printed circuit board 185 as taken along section line 8-8 in FIG. 7A, wherein the feedthru 155 is shown connected to the board 185. As can be understood from FIGS. 7A-8, when the feedthru 155 is properly coupled to the printed circuit board 185 such that the interfaces 190, 400 are properly aligned and in abutting planar contact with each other, the feedthru 155 is in electrical communication with the electrical components 180 of the board 185. More specifically, the can wall 65, which is electrically coupled to the feedthru housing 210, is in electrical communication with the ground side of the board 185 via the electrical pathway extending along the wires 225, traces 271, 325 and along the conductors or traces 335 extending to the ground side of each component 180. Similarly, the feedthru wire 160 is in electrical communication with the power side of the board 185 via the electrical pathway extending along the wire traces 270, 325 and along conductors or traces 330 extending to the power side of each component 180.

Figure 2:
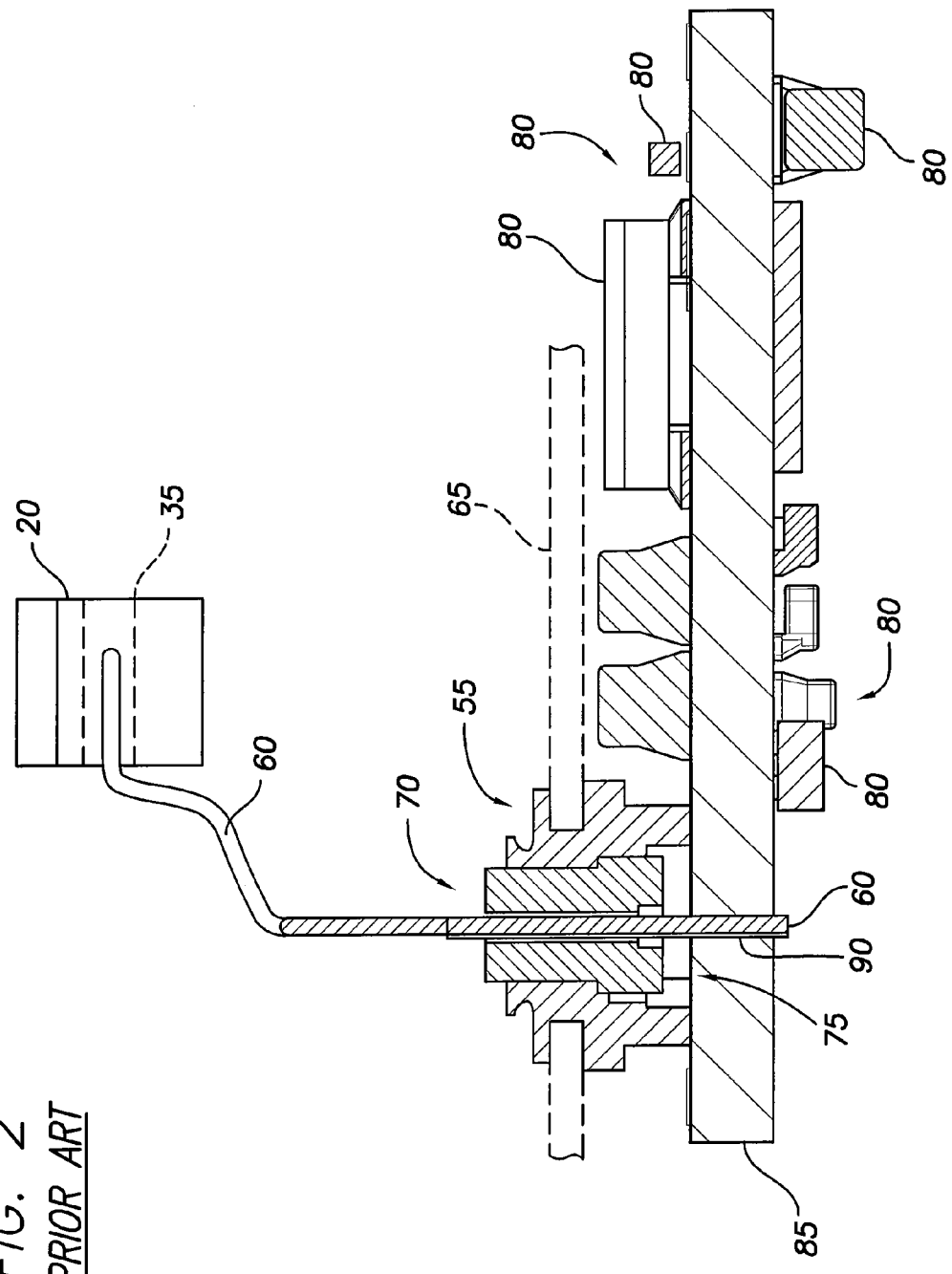
FIG. 2 is a cross-sectional elevation of one of the prior art feedthrus of FIG. 1A or 1B.

As discussed previously, the feedthru 155 can be placed in any orientation on a printed circuit board 185 such that the conductive traces 271, 270 of the feedthru interface 190 maintain electrical contact with corresponding traces 320, 325 of the interface 400 of the printed circuit board 185. As a comparison of FIGS. 2 and 8 shows, the feedthru 155 does not require a through-hole or use through-hole assembly technology. Instead, the feedthru 155 disclosed herein is configured to allow pick and place technology, thus reducing manufacturing costs by increasing efficiency and production speed via a higher degree of automation. Because the feedthru 155 does not require a through-hole, space on the opposite side of the board may be utilized for other components 180. This may allow for a printed circuit board with a reduced size. Additionally, the layers of flex of the circuit board are not penetrated. Also, because the printed circuit board may be a ceramic, it protects the relatively low melting point solder from melting and breaking electrical connections. Further, the feedthru 155 electrically shields the feedthru wire 160 and prevents RF radiation from escaping and interfering with other electrical components.

Although the present invention has been described with reference to preferred embodiments, persons skilled in the art will recognize that changes may be made in form and detail without departing from the spirit and scope of the invention.

What is claimed is:

1. A method of manufacturing an implantable pulse generator, the method comprising:
    providing a header and a can;
    extending a feedthru between the header and the can, the feedthru having a header side, a can side, and a feedthru wire, the can side having a first generally planar electrically conductive interface, the feedthru wire having a header end and a can end, and the feedthru wire extending through the feedthru from the first interface to project from the header side into the header;
    disposing an electrical component inside the can, the electrical component having a side abutted and attached to the can side such that the side of the electrical component covers the can end of the feedthru wire, and the side of the electrical component having a second generally planar electrically conductive interface; and
    placing the interfaces in physical contact with each other.

2. The method of claim 1, wherein the interfaces are placed in physical contact via a pick-and-place process.

3. The method of claim 1, wherein the electrical component comprises at least one of a hybrid, output flex and printed circuit board.

4. The method of claim 3, wherein the first generally planar electrically conductive interface comprises a power electrical trace and a ground electrical trace spaced apart from each other, and the second generally planar electrically conductive interfaces comprises a power electrical trace and a ground electrical trace spaced apart from each other.

5. The method of claim 4, wherein placing the interfaces in physical contact causes the power electrical traces to abut and the ground electrical traces to abut.

6. The method of claim 1, wherein the first generally planar electrically conductive interface comprises a first electrically conductive trace electrically coupled with the can end of the feedthru wire, the second generally planar electrically conductive interface comprises a second electrically conductive trace electrically coupled with a power side of the electrical component, and the first and second traces are in abutting electrical contact.

7. The method of claim 6, wherein the first generally planar electrically conductive interface further comprises a third electrically conductive trace electrically coupled with a ground side of the feedthru, the second generally planar electrically conductive interface further comprises a second electrically conductive trace electrically coupled to a ground side of the electrical component, and the first and second traces are in abutting electrical contact.

8. The method of claim 7, wherein at least one of the traces comprises a recessed portion that is at least one of generally recessed relative to the rest of the first electrical trace and generally recessed relative to the rest of the generally planar electrically conductive interfaces.

9. The method of claim 7, wherein at least one of the traces comprises a border that is arcuate along at least a portion thereof.

10. The method of claim 7, wherein the traces of at least one of the generally planar electrically conductive interfaces form concentric circles.

\* \* \* \* \*